United States Patent [19]

Hoehn et al.

[11] 4,062,858
[45] Dec. 13, 1977

[54] DERIVATIVES OF 5,6-DIHYDROBENZO[5,6]CYCLOHEPTA[1,2-b]PYRAZOLO[4,3-e]PYRIDIN-11(1H)-ONES AND 11(1H)-IMINES

[75] Inventors: Hans Hoehn, Tegernheim, Germany; Jack Bernstein, New Brunswick, N.J.; B. Richard Vogt, Yardley, Pa.

[73] Assignee: E. R. Squibb & Sons, Inc., Princeton, N.J.

[21] Appl. No.: 753,116

[22] Filed: Dec. 22, 1976

[51] Int. Cl.$^2$ .................................. C07D 471/22
[52] U.S. Cl. ...................... 260/296 P; 260/268 PC; 260/293.6; 260/295 F; 260/296 H; 424/246; 424/248.56; 424/250; 424/256; 424/267; 424/248.57; 544/58; 544/60; 544/125
[58] Field of Search ....... 260/296 P, 293.6, 247.5 EP; 424/263, 267

[56] References Cited

U.S. PATENT DOCUMENTS

| | | | |
|---|---|---|---|
| 3,720,675 | 3/1973 | Hoehn et al. | 260/293.6 |
| 3,987,051 | 10/1976 | Denzei et al. | 260/293.6 |
| 4,018,779 | 4/1977 | Hoehn et al. | 260/296 P |

OTHER PUBLICATIONS

Villani et al. J Heterocycl. Chem. 1971, vol. 8, pp. 73–81.

*Primary Examiner*—Natalie Trousof
*Attorney, Agent, or Firm*—Lawrence S. Levinson; Merle J. Smith

[57] ABSTRACT

New derivatives of 5,6-dihydrobenzo[5,6]cyclohepta[1,2-b]pyrazolo[4,3-e]pyridin-11(1H)-ones and imines, respectively, have the general formula

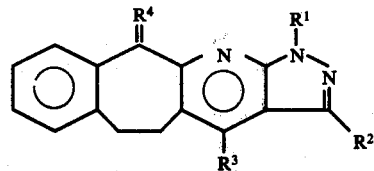

They and the salts thereof are useful as psychotropic and antiinflammatory agents.

17 Claims, No Drawings

DERIVATIVES OF 5,6-DIHYDROBENZO[5,6]CYCLOHEPTA[1,2-B]PYRAZOLO[4,3-E]PYRIDIN-11(1H)-ONES AND 11(1H)-IMINES

SUMMARY OF THE INVENTION

This invention relates to new derivatives of 5,6-dihydrobenzo[5,6]cyclohepta[1,2-b]pyrazolo[4,3-e]-pyridin-11(1H)-ones and imines and salts thereof. These new compounds have the general formula

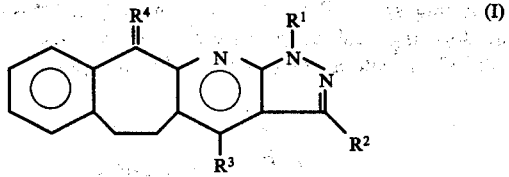

$R^1$ is lower alkyl, phenyl or phenyl-lower alkyl;
$R^2$ is hydrogen, lower alkyl or phenyl;
$R^3$ is hydroxy, lower alkoxy, halogen or an amine group.

The amine group is either an acyclic group

wherein $R^5$ and $R^6$ each is hydrogen, lower alkyl or phenyl or $R^5$ and $R^6$ taken together with the nitrogen form a monocyclic nitrogen heterocyclic of 5 or 6 members in which an additional nitrogen, oxygen or sulfur may be present.

$R^4$ is oxygen (=O) or substituted imine (=NR)
R is lower alkyl or phenyl.

DETAILED DESCRIPTION OF THE INVENTION

This invention relates to new compounds which are substituted 5,6-dihydrobenzo[5,6]cyclohepta[1,2-b]-pyrazolo[4,3-e]pyridines and are useful as psychotropic and antiinflammatory agents. After the ring system has been produced, treatment with various reagents sequentially or alternately as described more fully below yields the derivatives having the uses described.

These derivatives are more particularly 5,6-dihydrobenzo[5,6]cyclohepta[1,2-b]pyrazolo[4,3-e]pyridin-11 (1H)-ones and 5,6-dihydrobenzo[5,6]cyclohepta[1,2-b]pyrazolo[4,3-e]pyridin-11(1H)imines which are substituted in the 1- and 4-positions and optionally substituted in the 3-position. The new class of compounds have the general formula

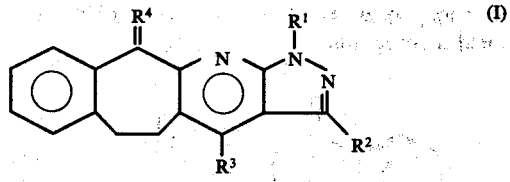

This class is characterized by two principal substituent groups, i.e., $R^4$ is oxo or $R^4$ is a substituted imine group, and these compounds have the following formulas, respectively:

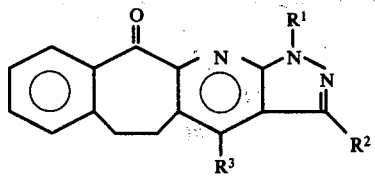

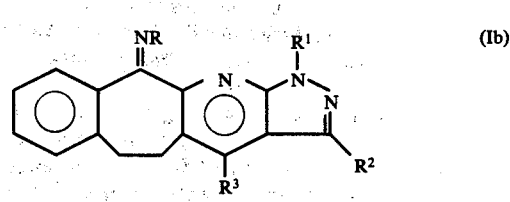

The various derivatives are described in greater detail in the description of the method of synthesis and in the specific examples which follow. All of these compounds are within the scope of this invention.

The symbols have the following meanings which are the same throughout this specification.

$R^1$ is lower alkyl, phenyl or phenyl-lower alkyl.

The lower alkyl groups are straight or branched chain hydrocarbon groups having up to seven carbon atoms like methyl, ethyl, propyl, isopropyl, butyl, isobutyl, t-butyl, pentyl and the like. The phenyl-lower alkyl groups are of the same type having a phenyl substituent attached to the alkyl chain. In each instance, the $C_1$-$C_4$ alkyl groups and especially the $C_1$-$C_2$ alkyl groups are preferred.

$R^2$ is hydrogen, lower alkyl or phenyl.

The lower alkyl groups represented by $R^2$ are of the same kind as described above with the same preferences for $C_1$-$C_4$ and $C_1$-$C_2$ members.

$R^3$ is hydroxy, lower alkoxy, halo or an amine group

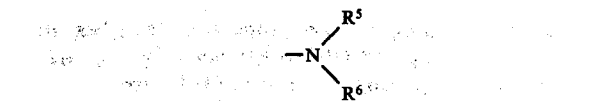

The lower alkoxy groups are of the same type as the lower alkyl groups having such lower alkyl groups linked to an oxygen atom, e.g., methoxy, ethoxy, propoxy, isopropoxy, butoxy, t-butoxy and the like. The $C_1$-$C_4$ and especially the $C_1$-$C_2$ lower alkoxy groups are similarly preferred. The halogens represented by $R^3$ include the four common halogens, preferably chlorine and bromine, especially chlorine.

The amine group $$-N\begin{matrix}R^5\\R^6\end{matrix}$$

represented by $R^3$ is an acyclic amine group wherein $R^5$ is hydrogen, lower alkyl or phenyl and $R^6$ is lower alkyl or phenyl or $R^5$ and $R^6$ join with the nitrogen to form a monocyclic heterocyclic having 5 or 6 members in which there may be an additional hetero atom which is oxygen, sulfur or nitrogen, the remaining atoms being carbon. The heterocyclic is unsubstituted or substituted with a lower alkyl or hydroxy-lower alkyl group.

The acyclic amine groups represented by

include, for example, lower alkylamino, e.g., methylamino, ethylamino, propylamino, isopropylamino, butylamino, t-butylamino and the like or phenylamino, di(lower alkyl)-amino, e.g., dimethylamino, diethylamino, methylethylamino, dipropylamino, dibutylamino and the like, anilino, etc. The preferences for $C_1$-$C_4$ and especially $C_1$-$C_2$ alkyl groups apply in this instance also. Only one of $R^5$ and $R^6$ is phenyl.

The heterocyclic substituents represented by the group

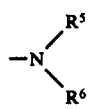

include particularly piperidino, morpholino, thiamorpholino and piperazino each of which can bear a lower alkyl or hydroxy-lower alkyl group, i.e., $R^7$-hetero in which the "hetero" is one of those heterocyclics named and $R^7$ is hydrogen when unsubstituted and lower alkyl or hydroxy-lower alkyl when substituted. 4-Methylpiperidino, 4-methylpiperazino and 4-hydroxyethylpiperazino are exemplary substituted members and preferred.

$R^4$ is oxo (=O) or substituted imino (=NR). R is lower alkyl of the type described above or phenyl.

Especially preferred compounds are those compounds of formula Ia wherein $R^1$ is lower alkyl, particularly ethyl; $R^2$ is hydrogen; and $R^3$ is hydroxy, lower alkoxy, particularly methoxy and ethoxy, or lower alkylamino particularly methylamino and butylamino; and those compounds of formula Ib wherein $R^1$ is lower alkyl particularly ethyl; $R^2$ is hydrogen; $R^3$ is lower alkylamino, particularly methylamino and butylamino and R is lower alkyl, particularly methyl and butyl.

The new compounds of this invention are prepared by the following series of reactions.

A 5-aminopyrazole of the formula

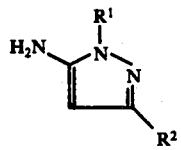

[prepared according to the procedure described in Z.f.Chemie 10, 386–388 (1970)] is reacted with a 2-(2-phenylethyl)-acetoacetic acid ester of the formula

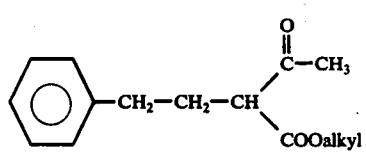

[prepared according to the procedure described in Annalen der Chemie 395, 95 (1913)], by heating at a temperature of about 140° C. in the presence of polyphosphoric acid producing a compound of the formula

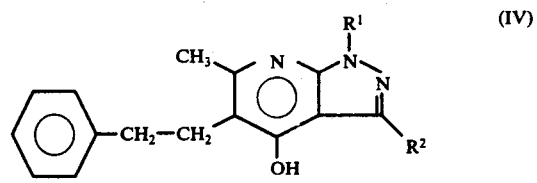

This intermediate of formula IV is oxidized with an oxidizing agent like selenium dioxide in a solvent like diethyleneglycol dimethyl ether or pyridine at about 140° C to yield a compound of the formula

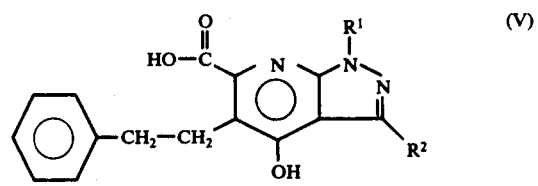

which in most cases contain, besides some unreacted compound of formula IV, the aldehyde of the formula

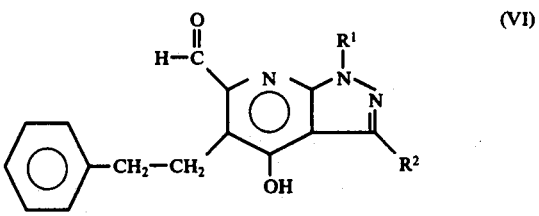

as impurities. Both can be separated by conventional methods. The methyl compound of formula IV can be used again in the oxidation step while the aldehyde of the formula VI is converted to the acid of the formula V by means of $H_2O_2$ in acetic acid.

The compound of formula V is then cyclized by heating at a temperature of about 210° using polyphosphoric acid as the ring closure agent, to produce a product of the formula

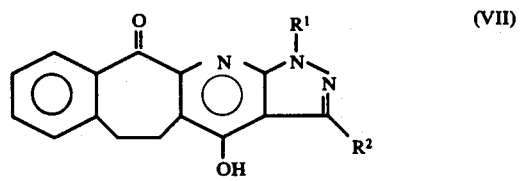

The tetracyclic heterocycle of the formula VII is treated with an inorganic acid chloride or bromide such as phosphorus oxychloride, thionyl chloride, etc., to yield a compound of the formula

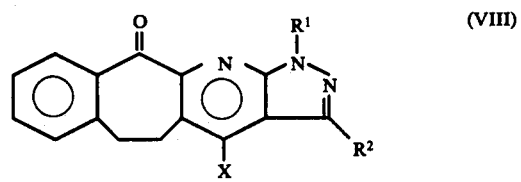

wherein X is chlorine or bromine.

Treatment of the compound of formula VIII with a primary amine of the formula

R—NH₂ (IX)

produces the amino derivative of the formula

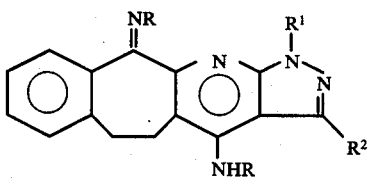

which can be hydrolyzed by means of aqueous acid like sulfuric acid to a compound of the formula

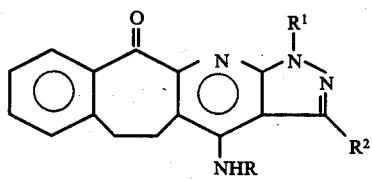

When a compound of formula VIII is made to react with a secondary amine of the formula

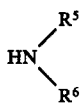

a product of the formula

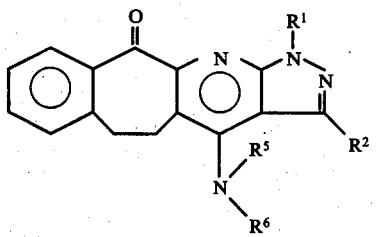

is obtained.

Compounds wherein $R^3$ is lower alkoxy, according to the formula

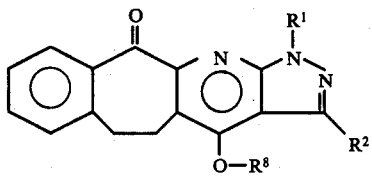

wherein $R^8$ is lower alkyl, are prepared by alkylating the hydroxy derivative of formula VII with a lower alkyl halide in the presence of a base like potassium carbonate. The halide is preferably the chloride or bromide. Alternatively, a compound of the formula VIII can be treated with an appropriate alcoholate, e.g., a metal alcoholate like sodium ethoxide, potassium methoxide or the like to yield the same product.

The new compounds of formula I form salts which are also part of this invention. The salts include acid addition salts, particularly the non-toxic, physiologically acceptable members. These salts are formed by reaction with one or more equivalents of any of a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate or aryl- or alkanesulfonates like benzenesulfonate, methanesulfonate, cyclohexanesulfamate and toluenesulfonate. The acid addition salts frequently provide a convenient means for isolating the product, e.g., by forming an precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with one or more equivalents of acid containing the desired anion.

Certain members, e.g., those compounds of formula I wherein $R^3$ is hydroxy, form salts with metals, e.g., alkali metals like sodium, alkaline earth metals like calcium and magnesium, etc. $R_3$ then becomes —O—Met—, wherein Met represents the metal ion. The alkali metals, sodium and potassium in particular, are preferred in this instance. These salts can be used to form soluble derivatives or as intermediates.

Additional experimental details are found in the examples.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 1 to 25 mg. per kilogram per day, preferably 2 to 20 mg. per kilogram per day, in single or 2 to 4 divided doses, as indicated by the carageenan edema assay in rats.

The new compounds of this invention are also psychotropic agents and can be used as ataractic agents for the relief of anxiety and tension states, for example, in mice, cats, rats, dogs and other mammalian species. For this purpose a compound or mixture of compounds of formula I, or non-toxic, physiologically acceptable salt thereof, is preferably administered orally, but parenteral routes such as subcutaneously, intramuscularly, intravenously or intraperitoneally can also be employed. A single dose, or preferably 2 to 4 divided daily doses, provided on a basis of about 10 to 100 mg. per kilogram per day, preferably about 5 to 25 mg. per kilogram per day, is appropriate.

The compounds of the invention can be utilized by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and constitute preferred embodiments. They also serve as models for the preparation of other members of the group which can be produced by suitable substitu-

EXAMPLE 1

1-Ethyl-5,6-dihydro-4-hydroxybenzo[5,6]cyclohepta[1,2-b]-pyrazolo[4,3-e]pyridin-11(1H)-one a. 1-Ethyl-6-methyl-5-(2-phenylethyl)-1H-pyrazolo[3,4-b]-pyridin-4-ol 33 g. of 5-amino-1-ethylpyrazole (0.3 mol.) in 310 g. of polyphosphoric acid are heated to 80° (bath temperature). While stirring, 70.5 g. of 2-(2-phenylethyl)acetoacetic acid, ethyl ester (0.3 mol.) are added to the mixture. The bath temperature is increased to 100°, the temperature of the solution rising to about 130°. As soon as the reaction temperature begins to drop the bath temperature is elevated to 140° and maintained for 45 minutes. After the mixture has cooled to room temperature, 650 ml. of water are added in portions and stirring is continued until the polyphosphoric acid is dissolved. The the aqueous phosphoric acid solution is decanted and the undissolved residue is treated with 400 ml. of 5% aqueous ammonia to neutralize the mixture. The mixture is extracted with chloroform and the chloroform extract is washed with water and dried with Na$_2$SO$_4$. Addition of ether precipitates 37 g. (44%) of 1-ethyl-6-methyl-5-(2-phenylethyl)-1H-pyrazolo[3,4-b]pyridin-4-ol; m.p. 251°–256°. Recrystallization from ethanol raises the m.p. to 258°–260°.

b. 1-Ethyl-4-hydroxy-5-(2-phenylethyl)-1H-pyrazolo[3,4-b]-pyridine-6-carboxylic acid and 1-ethyl-4-hydroxy-5-(2-phenylethyl)-1H-pyrazolo[3,4-b]pyridine-6-carboxaldehyde, hydrochloride (1:1)

To a suspension of 45 g. of 1-ethyl-6-methyl-5-(2-phenylethyl)-1H-pyrazolo[3,4-b]pyridin-4-ol (0.16 mol.) in 300 ml. of dry pyridine, 44 g. of well pulverized selenium dioxide are added with stirring. The mixture is heated at 130°–140° (bath temperature) for 15 hours. After cooling, the precipitated selenium is filtered off and the filtrate evaporated in vacuo. The remaining oil is stirred with 400 ml. of water and 400 ml. of ether, whereupon 16 g. of the starting material are precipitated. Then the aqueous solution is separated from ether, treated with charcoal and acidified with half concentrated aqueous hydrochloric acid. The precipitated 1-ethyl-4-hydroxy-5-(2-phenylethyl)-1H-pyrazolo[3,4-b]pyridine-6-carboxylic acid is filtered off, dried in a desiccator over P$_2$O$_5$ and finally in a drying oven at 100°, yield: 11.7 g. (23.5%); m.p. 250°–251° (ethanol).

The separated ethereal solution is treated with charcoal and dried with Na$_2$SO$_4$. Addition of ethereal hydrochloric acid precipitates the hydrochloride of 1-ethyl-4-hydroxy-5-(2-phenylethyl)-1H-pyrazolo[3,4-b]-pyridine-6-carboxaldehyde; yield: 9.2 g. (17%); m.p. 255°–257° (dec.) (acetonitrile).

Recrystallization of the carboxaldehyde from ethanol furnishes the acetal, 6-(diethoxymethyl)-1-ethyl-4-hydroxy-5-(2-phenylethyl)-1H-pyrazolo[3,4-b]pyridine hydrochloride (1:1); m.p. 160°–162° (ethylacetate/abs. ethanol).

c. 1-Ethyl-4-hydroxy-5-(2-phenylethyl)-1H-pyrazolo[3,4-b]-pyridine-6-carboxylic acid from the carboxaldehyde 16.5 g. of 1-ethyl-4-hydroxy-5-(2-phenylethyl)-1H-pyrazolo[3,4-b]pyridine-6-carboxaldehyde, hydrochloride (1:1) (0.05 mol.) are dissolved in 150 ml. of boiling glacial acetic acid. To the filtered solution, cooled to about 30°, 10 g. of H$_2$O$_2$ (35%) (0.1 mol.) are added in two portions and the mixture is allowed to stand for 20 hours at room temperature. The crsytallized 1-ethyl-4-hydroxy-5-(2-phenylethyl)-1H-pyrazolo[3,4-b]pyridine-6-carboxylic acid is filtered off, washed with acetic acid and ether, yield: 10.1 g. (65%); m.p. 250°–251° (ethanol).

d. 1-Ethyl-5,6-dihydro-4-hydroxybenzo[5,6]cyclohepta[1,2-b]-pyrazolo[4,3-e]pyridin-11 (1H)-one 12.4 g. of 1-ethyl-4-hydroxy-5-(2-phenylethyl)-1H-pyrazolo[3,4-b]pyridine-6-carboxylic acid (0.04 mol.) and 150 g. of polyphosphoric acid are heated at 200°–210° (bath temperature) with stirring for 30 minutes. After the mixture has cooled to room temperature 300 ml. of water are added slowly with stirring until the polyphosphoric acid is completely dissolved. The remaining 1-ethyl-5,6-dihydro-4-hydroxybenzo[5,6]cyclohepta[1,2-b]pyrazolo[4,3-e]pyridin-11 (1H)-one is dissolved in chloroform, the extract is washed twice with water, dried with Na$_2$SO$_4$ and then evaporated in vacuo, yield: 9 g. (77%); m.p. 190°–192°. Recrystallization from ethanol raises the m.p. to 195°–197°.

EXAMPLE 2

4-Chloro-1-ethyl-5,6-dihydrobenzo[5,6]cyclohepta[1,2-b]-pyrazolo[4,3-e]pyridin-11 (1H)-one 41 g. of 1-ethyl-5,6-dihydro-4-hydroxybenzo[5,6]-cyclohepta[1,2-b]pyrazolo[4,3-e]pyridin-11 (1H)-one (0.14 mol.) and 350 ml. of phosphorus oxychloride are refluxed for 4.5 hours. After cooling, the solution is filtered, the excess phosphorus oxychloride is removed in vacuo and the residue treated with water and extracted with chloroform. The chloroform extract is washed twice with water, dried with Na$_2$SO$_4$, treated with charcoal and then evaporated in vacuo to give 38 g. (87%) of 4-chloro-1-ethyl-5,6-dihydrobenzo[5,6]-cyclohepta[1,2-b]pyrazolo[4,3-e]pyridin-11(1H)-one; m.p. 156°–159° (recrystallized from ethanol).

EXAMPLE 3

4-Ethoxy-1-ethyl-5,6-dihydrobenzo[5,6]cyclohepta[1,2-b]-pyrazolo[4,3-e]pyridin-11(1H)-one 6.2 g. of 4-chloro-1-ethyl-5,6-dihydrobenzo[5,6]-cyclohepta[1,2-b]pyrazolo[4,3-e]pyridin-11(1H)-one (0.02 mol.) are added to a solution of 0.5 g. of sodium (0.022 mol.) in 150 ml. of absolute ethanol. The mixture is heated at 120° (bath temperature) in an autoclave for four hours. After cooling, the crystallized 4-ethoxy-1-ethyl-5,6-dihydrobenzo[5,6]cyclohepta[1,2-b]pyrazolo[4,3-e]-pyridin-11(1H)-one is filtered off and washed with water; yield: 3.5 g. An additional crop of 2.1 g. is obtained by work up of the mother liquor, total yield: 5.6 g. (87.5%). m.p. 150°–152° (recrystallized from ethanol).

EXAMPLE 4

1-Ethyl-5,6-dihydro-4-methoxybenzo[5,6]cyclohepta[1,2-b]-pyrazolo[4,3-e]pyridin-11(1H)-one When sodium ethoxide in the procedure of Example 3 is replaced by sodium methoxide, 1-ethyl-5,6-dihydro-4-methoxybenzo[5,6]cyclohepta[1,2-b]pyrazolo[4,3-e]pyridin-11(1H)-one is obtained; yield; 73%, m.p. 197°–200° (abs. ethanol).

EXAMPLE 5

1-Ethyl-1,5,6,11-tetrahydro-N-methyl-11-(methylimino)benzo[5,6]cyclohepta[1,2-b]pyrazolo[4,3-e]pyridin-4-amine 7.7 g. of 4-chloro-1-ethyl-5,6-dihydrobenzo[5,6]-cyclohepta[1,2-b]pyrazolo[4,3-e]pyridin-11('H)-one (0.025 mol.) and 100 ml. of alcoholic methylamine solution (127 g/l) are heated at 150° (bath temperature) in an autoclave for 5.5 hours. After cooling, the solution is filtered, evaporated in vacuo, the residue treated with water and collected. Then the product is agitated with ether in order to dissolve starting material and the purified 1-ethyl-1,5,6,11-tetrahydro-N-methyl-11-(methylimino)benzo[5,6]cyclohepta[1,2-b]pyrazolo[4,3-e]pyridin-4-amine is washed with water, then with ether and dried in a desiccator over $P_2O_5$, yield: 6.2 g. (78%); m.p. 233°-235° (acetone).

EXAMPLE 6

1-Ethyl-5,6-dihydro-4-(methylamino)benzo[5,6]cyclohepta[1,2-b]pyrazolo[4,3-e]pyridin-11 (1H)-one 6.4 g. of 1-ethyl-1,5,6,11-tetrahydro-N-methyl-11-(methylimino)benzo[5,6]cyclohepta[1,2,-b]pyrazolo[4,3-e]-pyridin-4-amine (0.02 mol.) in 60 ml. of aqueous sulfuric acid (30%) are heated at 80° (bath temperature) for 8 hours with stirring. Then 40 ml. of water are added to the solution and the mixture is treated with charcoal, filtered and neutralized by adding dropwise concentrated aqueous ammonia under ambient cooling. The precipitated 1-ethyl-5,6-dihydro-4-(methylamino)benzo[5,6]cyclohepta[1,2-b]pyrazolo[4,3-e]pyridin-11(1H)-one is stirred until the compound becomes crystalline. The collected product weighs 5.5 g. (90%); m.p. 207°-209° (abs. ethanol).

The hydrochloride is prepared by dissolving the product in ether and adding, while stirring, ethereal hydrogen chloride.

EXAMPLE 7

N-Butyl-11-(butylimino)-1-ethyl-1,5,6,11-tetrahydrobenzo-[5,6]cyclohepta[1,2-b]pyrazolo[4,3-e]pyridin-4-amine 10.8 g. of 4-chloro-1-ethyl-5,6-dihydrobenzo[5,6]-cyclohepta[1,2-b]pyrazolo[4,3-e]pyridin-11(1H)-one (0.035 mol.) and 100 ml. of butylamine are reacted in an autoclave by the procedure of Example 5, yield: 9.8 g. (70%); m.p. 124°-125° (ether; refrigerator).

EXAMPLE 8

4-(Butylamino)-1-ethyl-5,6-dihydrobenzo[5,6]cyclohepta[1,2-b]-pyrazolo[4,3-e]pyridin-11(1H)-one 7.2 g. of N-butyl-11-(butylimino)-1-ethyl-1,5,6,11-tetrahydrobenzo[5,6]cyclohepta[1,2-b]pyrazolo[4,3-e]-pyridin-4-amine (0.018 mol.) and 100 ml. of aqueous sulfuric acid (30%) are reacted according to the procedure of Example 6, yield: 4.7 g. (75%); m.p. 181°-183° (ethyl acetate/ether).

EXAMPLE 9

4-Butoxy-1-ethyl-5,6-dihydrobenzo[5,6]cyclohepta[1,2-b]-pyrazolo[4,3-e]pyridin-11(1H)one When the sodium ethoxide in the procedure of Example 3 is replaced by sodium butoxide, 4-butoxy-1-ethyl-5,6-dihydrobenzo[5,6]cyclohepta[1,2-b]pyrazolo[4,3-e]pyridin-11(1H) one is obtained.

EXAMPLE 10

1-Benzyl-5,6-dihydro-4-hydroxybenzo[5,6]cyclohepta[1,2-b]-pyrazolo[4,3-e]pyridin-11(1H) one By substituting 5-amino-1-benzylpyrazole for the 5-amino-1-ethylpyrazole in the procedure of Example 1, 1-benzyl-5,6-dihydro-4-hydroxybenzo[5,6]cyclohepta[1,2-b]-pyrazolo[4,3-e]pyridin-11 (1H) one is obtained.

EXAMPLE 11

1-Benzyl-4-bromo-5,6-dihydrobenzo[5,6]cyclohepta[1,2-b]-pyrazolo[4,3-e]pyridin-11 (1H) one By treating the product of Example 10 according to the procedure of Example 2, but substituting phosphorus oxybromide for the phosphorus oxychloride, 1-benzyl-4-bromo-5,6-dihydrobenzo[5,6]cyclohepta[1,2-b]pyrazolo[4,3-e]-pyridin-11(1H)one is obtained.

EXAMPLE 12

1-Benzyl-4-propoxy-5,6-dihydrobenzo[5,6]cyclohepta[1,2-b]pyrazolo[4,3-e]pyridin-11(1H)one By treating the product of Example 11 according to the procedure of Example 3, replacing the sodium ethoxide with sodium propoxide, 1-benzyl-4-propoxy-5,6-dihydrobenzo[5,6]cyclohepta[1,2-b]pyrazolo[4,3-e]pyridin-11(1H)one is obtained.

EXAMPLE 13

1-Methyl-3-phenyl-4-hydroxy-5,6-dihydrobenzo[5,6]-cyclohepta[1,2-b]pyrazolo[4,3-e]pyridin-11(1H) one By substituting 5-amino-1-methyl-3-phenylpyrazole for the 5-amino-1-ethylpyrazole in the procedure of Example 1, 1-methyl-3-phenyl-4-hydroxy-5,6-dihydrobenzo-[5,6]cyclohepta[1,2-b]pyrazolo[4,3-e]pyridin-11(1H)one is obtained.

EXAMPLE 14

4-Methylamino-1-phenyl-5,6-dihydrobenzo[5,6]cyclohepta[1,2-b]pyrazolo[4,3-e]pyridin-11 (1H)one By substituting 5-amino-1-phenylpyrazole for the 5-amino-1-ethylpyrazole in the procedure of Example 1 then continuing as in Examples 2, 3, 5 and 6, 4-chloro-1-phenyl-5,6-dihydrobenzo[5,6]cyclohepta[1,2-b]pyrazolo-[4,3-e]pyridin-11(1H)one, 4-ethoxy-1-phenyl-5,6-dihydrobenzo[5,6]cyclohepta[1,2-b]pyrazolo[4,3-e]pyridin-11(1H)-one, 1-phenyl-1,5,6,11-tetrahydro-N-methyl-11-(methylimino)-benzo[5,6]cyclohepta[1,2-b]pyrazolo[4,3-e]pyridin-4-amine and 4-methylamino-1-phenyl-5,6-dihydrobenzo[5,6]cyclohepta-[1,2-b]pyrazolo[4,3-e]pyridin-11(1H)-one, respectively, are obtained.

EXAMPLE 15

1-Benzyl-4-(phenylamino)-5,6-dihydrobenzo[5,6]cyclohepta-[1,2-b]pyrazolo[4,3-e]pyridin-11(1H)one By substituting the 1-benzyl-4-bromo-5,6-dihydrobenzo[5,6]cyclohepta[1,2-b]pyrazolo[4,3-e]pyridin-11(1H)one of Example 11 in the procedure of Example 5 and substituting aniline for the methylamine and continuing as in Example 6, 1-benzyl-1,5,6,11-tetrahydro-N-phenyl-11-(phenylimino)benzo-[5,6]cyclohepta[1,2-b]pyrazolo[4,3-e]pyridin-4-amine and 1-benzyl-4-(phenylamino)-5,6-dihydrobenzo[5,6]-cyclohepta[1,2-b]pyrazolo[4,3-e]pyridin-11(1H) one, respectively, are obtained.

EXAMPLE 16

4-Diethylamino)-1-ethyl-5,6-dihydrobenzo[5,6]cyclohepta[1,2-b]pyrazolo[4,3-e]pyridin-11 (1H)one By substituting diethylamine for the methylamine in the procedure of Example 5,4-(diethylamino)-1-ethyl-5,6-dihydrobenzo[5,6]cyclohepta[1,2-b]pyrazolo[4,3-e]-pyridin-11(1H)one is obtained.

EXAMPLE 17

4-Piperidino-1-ethyl-5,6-dihydrobenzo-[5,6]cyclohepta[1,2-b]pyrazolo[4,3-e]pyridin-11(1H)one By substituting piperidine for the methylamine in the procedure of Example 5, 4-piperidino-1-ethyl-5,6-dihydrobenzo[5,6]cyclohepta[1,2-b]pyrazolo[4,3-e]pyridin-11(1H) one is obtained.

EXAMPLE 18

4-(4-Methylpiperazino)-1-ethyl-5,6-dihydrobenzo[5,6]-cyclohepta[1,2-b]pyrazolo[4,3-e]pyridin-11(1H)one By substituting 1-methylpiperazine for the methylamine in the procedure of Example 5, 4-(4-methylpiperazino)-1-ethyl-5,6-dihydrobenzo[5,6]cyclohepta[1,2-b]pyrazolo[4,3-e]pyridin-11(1H)one is obtained.

EXAMPLE 19

1-Phenylethyl-5,6-dihydro-4-(methylamino)benzo[5,6]-cyclohepta[1,2-b]pyrazolo[4,3e]pyridin-11(1H)-one By substituting 5-amino-1-phenylethylpyrazole for the 5-amino-1-ethylpyrazole in the procedure of Example 1 and then continuing as in Examples 2, 3, 5 and 6, 4-hydroxy-1-phenylethyl-5,6-dihydrobenzo[5,6]cyclohepta-[1,2-b]pyrazolo[4,3-e]pyridin-11(1H)one, 4-chloro-1-phenylethyl-5,6-dihydrobenzo[5,6]cyclohepta[1,2-]pyrazolo-[4,3-e]pyridin-11(1H)-one, 4-ethoxy-1-phenylethyl-5,6-dihydrobenzo[5,6]cyclohetpa[1,2-b]pyrazolo[4,3-e]pyridin-11(1H)-one, N-methyl-1-phenylethyl-1,5,6,11-tetrahydro-11-(methylimino)benzo[5,6]cyclohepta[1,2-b]pyrazolo[4,3-e]pyridin-4-amine and 1-phenylethyl-5,6-dihydro-4-(methylamino)-benzo[5,6]cyclohepta[1,2-b]pyrazolo[4,3-]pyridin-11(1H)one respectively, are obtained.

EXAMPLE 20

1,3-Dimethyl-5,6-dihydro-4-(ethylamino)benzo[5,6]cyclohepta[1,2-b]pyrazolo[4,3-e]pyridin-11(1H)one By substituting 5-amino-1,3-dimethylpyrazole for the 5-amino-1-ethylpyrazole in the procedure of Example 1 and then continuing as in Examples 2, 5 and 6, substituting ethylamine for the methylamine in the procedure of Example 5, 1,3-dimethyl-4-hydroxy-5,6-dihydrobenzo[5,6]cyclohepta-[1,2-b]pyrazolo[4,3-e]pyridine-11(1H)-one, 4-chloro-1,3-dimethyl-5,6-dihydrobenzo[5,6]cyclohepta[1,2-b]pyrazolo[4,3-e]pyridin-11(1H)-one, 1,3-dimethyl-4-ethoxy-5,6-dihydrobenzo[5,6]cyclohepta[1,2-b]pyrazolo[4,3-e]pyridin-11(1H)-one, 1,3-dimethyl-N-ethyl- 1,5,6,11-tetrahydro-11-(ethylimino)benzo[5,6]cyclohepta[1,2-b]pyrazolo[4,3-e]-pyridin-4-amine, and 1,3-dimethyl-5,6-dihydro-4-(ethylamino)benzo[5,6]cyclohepta[1,2-b]pyrazolo[4,3-e]pyridin-11(1H)one, respectively, are obtained.

EXAMPLE 21

1-Benzyl-4-(dimethylamino)-5,6-dihydrobenzo[5,6]cyclohepta[1,2-b]pyrazolo[4,3-e]pyridin-11 (1H)one By substituting the product of Example 11 in the procedure of Example 5 and substituting dimethylamine for the methylamine, 1-benzyl-4-(dimethylamino)-5,6-dihydrobenzo[5,6]cyclohepta[1,2-b]pyrazolo[4,3-e]pyridin-11(1H)-one is obtained.

EXAMPLE 22

4-(4-Methylpiperidino)-1-ethyl-5,6-dihydrobenzo[5,6]-cyclohepta[1,2-b]pyrazolo[4,3-e]pyridin-11(1H)one By substituting 4-methylpiperidine for the methylamine in the procedure of Example 5, 4-(4-methylpiperidino)1-ethyl-5,6-dihydrobenzo[5,6]cyclohepta[1,2-b]pyrazolo[4,3-e]pyridin-11(1H)one is obtained.

EXAMPLE 23

1-Benzyl-4-(morpholino)-5,6-dihydrobenzo[5,6]cyclohepta-[1,2-b]pyrazolo[4,3-e]pyridin-11(1H)one By substituting the product of Example 11 in the procedure of Example 5 and substituting morpholine for the methylamine, 1-benzyl-4-(morpholino)-5,6-dihydrobenzo-[5,6]cyclohepta[1,2-b]pyrazolo[4,3-e]pyridin-11(1H)one is obtained.

EXAMPLE 24

1-Ethyl-4-thiamorpholino-5,6-dihydrobenzo[5,6]cyclohepta-[1,2-b]pyrazolo[4,3-e]pyridin-11(1H)one By substituting thiamorpholine for the methylamine in the procedure of Example 5, 1-ethyl-4-thiamorpholino-5,6-dihydrobenzo[5,6]cyclohepta[1,2-b]pyrazolo[4,3-e]-pyridin-11(1H)one is obtained.

EXAMPLE 25

1-Ethyl-4-[4-(2-hydroxyethyl)piperazino]-5,6-dihydrobenzo[5,6]cyclohepta[1,2-b]pyrazolo[4,3-e]pyridin-11(1H)one By substituting 4-(2-hydroxyethyl)piperazine for the methylamine in the procedure of Example 5, 1-ethyl-4-[4-(2-hydroxyethyl)piperazino]-5,6-dihydrobenzo[5,6]-cyclohepta[1,2-b]pyrazolo[4,3-e]pyridin-11(1H)one is obtained.

What is claimed is:

1. A compound of the formula

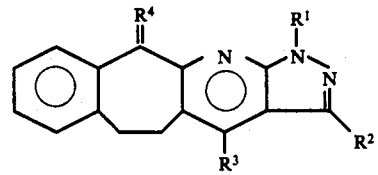

wherein
$R^1$ is lower alkyl, phenyl or phenyl-lower alkyl;
$R^2$ is hydrogen, lower alkyl or phenyl;
$R^3$ is hydroxy, lower alkoxy, halo or the group

wherein $R^5$ is hydrogen, lower alkyl or phenyl and $R^6$ is lower alkyl or phenyl, or

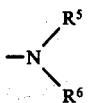

together is one of the unsubstituted heterocyclics piperidine or morpholine or one of said heterocyclics substituted with a lower alkyl or hydroxy-lower alkyl group;

$R^4$ is oxo, lower alkylimino or phenylimino; and physiologically acceptable salts thereof.

2. A compound as in claim 1 wherein $R^1$ is lower alkyl; $R^2$ is hydrogen; $R^3$ is hydroxy, lower alkoxy or lower alkylamino; and $R^4$ is oxo or lower alkylimino; and physiologically acceptable acid addition salts thereof.

3. A compound as in claim 1 wherein $R^4$ is oxo.

4. A compound as in claim 1 wherein $R^4$ is lower alkylimino.

5. A compound as in claim 1 wherein $R^3$ is lower alkylamino.

6. A compound as in claim 1 wherein $R^3$ is lower alkoxy.

7. A compound as in claim 1 wherein $R^3$ is hydroxy.

8. A compound as in claim 1 wherein $R^1$ is lower alkyl and $R^2$ is hydrogen.

9. A compound as in claim 1 wherein $R^1$ is ethyl and $R^2$ is hydrogen.

10. A compound as in claim 9 wherein $R^3$ is hydroxy and $R^4$ is oxo.

11. A compound as in claim 9 wherein $R^3$ is chloro and $R^4$ is oxo.

12. A compound as in claim 9 wherein $R^3$ is ethoxy and $R^4$ is oxo.

13. A compound as in claim 9 wherein $R^3$ is butylamino and $R^4$ is oxo.

14. A compound as in claim 9 wherein $R^3$ is methylamino and $R^4$ is oxo.

15. A compound as in claim 9 wherein $R^3$ is methoxy and $R^4$ is oxo.

16. A compound as in claim 9 wherein $R^4$ is methylimino and $R^3$ is methylamino.

17. A compound as in claim 9 wherein $R^4$ is butylimino and $R^3$ is butylamino.